(12) United States Patent
Holland (10) Patent No.: US 11,992,315 B2
(45) Date of Patent: May 28, 2024

(54) BLOOD SAMPLING DEVICE

(71) Applicant: Owen Mumford Limited, Woodstock (GB)

(72) Inventor: Damian Holland, Woodstock (GB)

(73) Assignee: Owen Mumford Limited, Oxfordshire (GB)

( * ) Notice: Subject to any disclaimer, the term of this patent is extended or adjusted under 35 U.S.C. 154(b) by 252 days.

(21) Appl. No.: 16/647,175

(22) PCT Filed: Sep. 27, 2018

(86) PCT No.: PCT/GB2018/052746
§ 371 (c)(1),
(2) Date: Mar. 13, 2020

(87) PCT Pub. No.: WO2019/064000
PCT Pub. Date: Apr. 4, 2019

(65) Prior Publication Data
US 2020/0268294 A1 Aug. 27, 2020

(30) Foreign Application Priority Data
Sep. 29, 2017 (GB) ..................................... 1715867

(51) Int. Cl.
*A61B 5/15* (2006.01)
*A61B 5/151* (2006.01)
(52) U.S. Cl.
CPC .. *A61B 5/150022* (2013.01); *A61B 5/150206* (2013.01); *A61B 5/150412* (2013.01);
(Continued)

(58) Field of Classification Search
CPC .... A61B 5/15–15003; A61B 5/150022; A61B 5/150206; A61B 5/150374;
(Continued)

(56) References Cited

U.S. PATENT DOCUMENTS 6,514,270 B1 2/2003 Schraga
2005/0234487 A1 10/2005 Shi
(Continued)

FOREIGN PATENT DOCUMENTS

CN 106963394 A 7/2017
EP 1359846 B1 11/2003
(Continued)

OTHER PUBLICATIONS

Search Report, related UK Application No. GB 1715867.6, dated Feb. 23, 2018, 2 pages.
(Continued)

*Primary Examiner* — Andrey Shostak
(74) *Attorney, Agent, or Firm* — Quarles & Brady LLP (57) ABSTRACT

A blood sampling device (1) comprising a housing (10) and a lancet (50). The housing has a fixed abutment surface for holdingly engaging the lancet in a rearward primed position. The blood sampling device further comprises a trigger (22) moveable from a rest position to a fire position to release the lancet for forward movement, wherein the trigger deflects the lancet body in a direction generally transverse to the longitudinal axis of the housing such that the lancet body may move forwardly past the fixed abutment surface.

20 Claims, 4 Drawing Sheets

(52) U.S. Cl.
CPC .. *A61B 5/150503* (2013.01); *A61B 5/150564* (2013.01); *A61B 5/150618* (2013.01); *A61B 5/150717* (2013.01); *A61B 5/150885* (2013.01); *A61B 5/15113* (2013.01); *A61B 5/15117* (2013.01); *A61B 5/15144* (2013.01)

(58) Field of Classification Search
CPC ..... A61B 5/150412; A61B 5/150503–150519; A61B 5/150534–150625; A61B 5/150564; A61B 5/150618; A61B 5/150717; A61B 5/150885; A61B 5/150916; A61B 5/15107–15117; A61B 5/15126–15132; A61B 5/15113; A61B 5/15144; A61B 5/15128

See application file for complete search history.

(56) References Cited

U.S. PATENT DOCUMENTS

| | | | |
|---|---|---|---|
| 2006/0229532 A1* | 10/2006 | Wong | A61B 5/150412 600/583 |
| 2008/0109025 A1 | 5/2008 | Yang et al. | |
| 2010/0274273 A1* | 10/2010 | Schraga | A61B 5/1411 606/172 |
| 2011/0196261 A1* | 8/2011 | Robbins | A61B 5/15194 600/583 |
| 2012/0203259 A1* | 8/2012 | Saeki | A61B 5/1513 606/182 |
| 2015/0313513 A1* | 11/2015 | Marshall | A61B 5/15194 606/182 |

FOREIGN PATENT DOCUMENTS

| | | |
|---|---|---|
| EP | 2859847 A1 | 4/2015 |
| GB | 2421439 A | 6/2006 |
| GB | 2434542 A | 8/2007 |
| GB | 2451840 A | 2/2009 |
| WO | 1998011821 A1 | 3/1998 |
| WO | 1998048696 A1 | 11/1998 |
| WO | 0078214 A1 | 12/2000 |
| WO | 2004103178 A1 | 12/2004 |
| WO | 2005020816 A1 | 3/2005 |
| WO | 2006067119 A2 | 6/2006 |
| WO | 2006110742 A2 | 10/2006 |
| WO | 2012093268 A1 | 7/2012 |
| WO | 2015116698 A1 | 8/2015 |

OTHER PUBLICATIONS

International Search Report and Written Opinion of the International Searching Authority from corresponding PCT Application No. PCT/GB2018/052746, dated Nov. 26, 2018 (12 pages).

* cited by examiner

BLOOD SAMPLING DEVICE

CROSS-REFERENCE TO RELATED APPLICATIONS

This application represents the U.S. National Stage of International Application No. PCT/GB2018/052746 filed Sep. 27, 2018, which claims priority to British Patent Application Serial No. GB 1715867.6, filed Sep. 29, 2017, and entitled, "A Blood Sampling Device", all of which are incorporated herein by reference in their entirety.

The present invention relates to blood sampling devices of the type which employ a sharp tip or needle to obtain a small sample of blood for testing purposes. Particularly, though not necessarily, the invention relates to blood sampling devices suitable for disposal after a single use.

Blood sampling is an important part of daily routine for some people and in many cases may even be employed at home wherein the user may self-administer and/or may not be a trained medical professional. Accordingly lancing devices are commonly used to provide a simple, reliable and repeatable method of collecting blood samples. Lancing devices are used to make a small incision at a sample site on the skin (typically for example a finger tip) to draw a sample of blood. Such devices may also be referred to as capillary blood sampling devices. Single use lancing devices are used for convenience and in order to reduce risk of infection and/or cross contamination between uses.

Known blood sampling devices employ a spring or other biasing member which forces a sharp skin piercing lancet tip into the sample site following triggering of the device. For convenience and clarity the skin piercing part of the lancet may generally be referred to herein in as a lancet "needle"; it will however be appreciated that this is non-liming and the lancet could be formed with any suitable incision member for example a generally cylindrical needle, a sharp edge or a blade element. Typically the lancet "needle" will be metal and the lancet will also include an injection moulded plastic lancet body.

Known lancet devices (particularly single use devices), such as the Applicant's Unistik® range of devices, typically comprise a housing containing the lancet and a firing mechanism. The firing mechanism is arranged to urge the lancet forward in use when the device is fired (via a trigger mechanism) such that lancet needle extends beyond the end of the housing. When fired, the sharp tip of the lancet protrudes forwardly of the housing through the aperture with sufficient force to puncture the skin of the user such that blood is drawn for a sample. Some single use lancing devices require the lancet to be cocked or primed before being released, while others are assembled and sold in the cocked condition, ready to fire. In either case, it is desirable that single use devices are simple and relatively cheap such that they provide the convenience and hygiene of being able to be disposed of after a single use. It is known to provide such single use lancing devices with a needle cap which is removable prior to use of the device. However, in some instances, if a user does not follow the written and visual instructions to twist the cap off they may force the cap off in a way that causes the device to malfunction. It would therefore be desirable to improve the safety of such devices to reduce the risk of accidental triggering.

A common cause of accidental triggering in prior art devices is the 'cap pop indicator'. This is where upon initiation of removal of the safety cap, for example upon twisting of the safety cap, the link between the cap and the lancet body is partially severed, causing the cap to pop forwardly. This indicates to the user than the cap is ready to pull off even when the link between the safety cap and the lancet body is not fully severed. This suggests to the user that they can pull the cap forwardly to remove it from the device such that the lancet is ready to fire. If the link between the cap and the lancet body is not fully severed, and the user pulls the cap forwardly, this fires the lancet before the user has pressed the device against their skin.

WO 00/78214 discloses a single use lancing device having a removable safety cap and a housing comprising a trigger member. The rear end of the lancet has a hooked tongue that latches behind a transverse web on the housing preventing forward movement of the lancet until the trigger is depressed. Depression of the trigger deforms the hooked tongue on the lancet body so that it is no longer in abutment with the transverse web. If the trigger is depressed before or during removal of the cap and the user pulls the safety cap forwardly before it is fully severed from the lancet body, as described above, the lancet will be prematurely fired.

WO2012/093268 also discloses a single use lancing device having a removable safety cap and a housing comprising a trigger member. When the lancing device is assembled in an initial position with the safety cap covering the forward end of the needle, the lancet body prevents depression of the trigger member. Upon removal of the safety cap, the lancet body is urged forward to an intermediate position in which the trigger member can be depressed to fire the lancet. However, even though the trigger cannot be depressed when the lancing device is in the initial position, the user can still prematurely pull the cap forward before the link between the safety cap and the lancet body is fully severed, pulling the lancet body forwardly with it. This therefore pulls the lancet body out of alignment with the trigger member so that it can be depressed and the device can be prematurely actuated.

Premature activation of the lancet is a serious problem as it means that a high proportion of devices fire before being pressed against the skin of the user and are wasted. Furthermore, this premature activation may also result in the user attempting to re-set the device and fire it again.

More experienced users may realise that this is an issue and so end up rotating the cap many times to ensure that the connection between the cap and the lancet body is severed fully before pulling. This can be time consuming and require additional effort, decreasing the convenience for the user It would therefore be desirable to provide a single use lancing device that overcomes at least some of the described problems associated with prior art devices.

In accordance with a first aspect of the present invention, there is provided a blood sampling device comprising:
- a housing having a forward end with an opening therein;
- a lancet comprising a lancet body supporting a lancet needle at a forward end thereof, the lancet being moveable mounted within said housing;
- an urging member for urging the lancet forwardly, in use, relative to the housing between a rearward primed position in which the lancet needle is within the housing and a forward lancing position in which the tip of the lancet needle projects forwardly from the opening at the forward end of the housing; wherein
- said housing defines a passageway along which the lancet travels between the rearward primed position and the forward lancing position and the housing having a fixed abutment surface for holdingly engaging the lancet in the rearward primed position; and the device further comprising a trigger moveable from a rest position to a fire position to release the lancet for forward movement, wherein the trigger deflects at least a portion of the lancet body in a direction generally transverse to the longitudinal axis such that the lancet body may move forwardly past the fixed abutment surface.

By using a fixed abutment surface on the housing to retain the lancet in the rearward primed position, embodiments of the invention may provide a more stable and secure latching of the lancet in comparison to prior art devices in which a trigger member (which will generally be moveably mounted to the housing) being required to retain the lancet. This may be particularly advantageous in resisting any unintentional movement/release of the lancet during cap removal.

The fixed abutment may for example form a shelf or ledge which obstructs the lancet from entering a rearward end of the passageway within the housing. In order to release the lancet, the trigger may deflect the lancet momentarily laterally past and out of engagement with the abutment. The lancet may then be free to enter and travel along the passage under the drive of the urging member.

The trigger may additionally or alternatively deflect at least a portion of the lancet body angularly relative to the longitudinal axis The device further comprises a removable safety cap for at least partially covering the lancet tip. The removable safety cap may be configured to prevent firing of the device prior to removal of the safety cap from the lancet. The safety cap may inhibit or block deflection of the lancet by the trigger prior to removal.

Prior to removal the cap may supports the lancet body within the device such that it cannot be deflected transversely past the abutment. For example, the cap may comprise a portion which extends through the opening at the forward end of the housing and along the passageway to a rearward end at the lancet body (for example an end which is joined to the forward end of the lancet body). Said portion may prevent transverse movement of the lancet within the housing when the cap is attached thereto. For example the cap may be profiled such that it is supported in the passageway to prevent any lateral movement. Alternatively or additionally, the cap may act to form a support bridging between the forward end of the device; thus, for example the lancet may form a support aligned in a axial direction of the device which resists or prevent movement of the lancet off said axis.

The cap is removable in the pricking direction such that the cap may be withdrawn from the passageway to ready the device. The cap may require twisting prior to withdrawal in the pricking direction. The cap may have a graspable portion external to the housing. The cap may have a stem substantially within the housing. The diameter of the stem substantially corresponds to the diameter of the aperture.

The trigger may comprise an externally accessible portion and depression of the externally accessible portion moves the trigger from the rest position to the fire position. Movement of the trigger from the rest position to the fire position may be a generally transverse movement relative to the longitudinal axis.

The trigger may be mounted on the housing and may, for example be an integral component of the housing. The trigger may be formed by a hinged portion of the outer housing. Typically, the housing may be an integral moulding with two halves hinged together, the trigger being formed on one of the halves.

In some embodiments the device may further comprise means for preventing rearward movement of the lancet body from the lancing position to the primed position. For example, the passage may comprise a second abutment surface configured to prevent rearward movement of the lancet body from the lancing position to the primed position. The second abutment surface may be located sufficiently rearwardly of the aperture that the sharp tip of the lancet body is contained within the housing after use.

The lancet body may be further provided with a second abutment surface configured to cooperate with the second passage abutment surface to prevent rearward movement of the lancet body from the lancing position to the primed position.

The fixed abutment may comprise an abutment member formed on the passage and projecting into the passage.

The abutment member may comprise a front surface and a rear surface. The rear surface may be configured to engage the lancet body to prevent forward movement thereof from the primed to the lancing position. The front surface may be configured to engage the lancet body to prevent rearward movement thereof from the lancing position to the primed position.

The passage may further comprise a deflection surface positioned forwardly of the or each passage abutment surface. For example, the deflection surface may be positioned forwardly of the fixed abutment surface. In embodiments having a fixed abutment surface and a second abutment surface, the deflection surface may be positioned forwardly of the fixed abutment surface and the second abutment surface. The deflection surface may be configured to reorientate the lancet after the lancet passes the fixed abutment surface. The deflection surface may be arranged to deflect at least a portion of the lancet body angularly and/or transversely relative to the longitudinal axis. The lancet body may for example be deflected from a passage position to a blocked position in which the lancet body cannot move rearwardly back past the front surface of the abutment member.

The lancet body may comprise a deflection surface configured to cooperate with the housing deflection surface.

The lancet body may comprise at least one radial projection. The radial projection may have a front surface configured to engage the first passage abutment surface and a rear surface configured to engage the second passage abutment surface.

Typically, the housing may be substantially elongate. The passage may be a substantially linear passage. The urging device may be a drive spring, for example a linear acting drive spring (particularly a compression spring). In the first configuration the spring may be compressed.

During lancing the sharp tip of the lancet body momentarily projects through the aperture defined in the forward surface of the housing and then rebounds back into the housing.

These and other aspects of the present invention will be apparent from the following specific description, in which embodiments of the present invention are described, by way of examples only, and with reference to the accompanying drawings, in which:

Directional descriptors as used in the following description of the preferred embodiments of the present invention, such as "upper", "lower", "top", "bottom", "front", "rear", etc. relate to the invention when in the preferred orientation. However, it will be clear to the skilled person that the device may be in any orientation and therefore the directional descriptors would be changed accordingly.

Front as used herein will be understood to refer to the end of the lancing device (or components thereof) which, in use, are closest to the sample site end of the device (i.e. the end which is pointed at the skin). Rear as used herein will be understood to refer to the end of the lancing device (or components thereof) which, in use, are furthest from the sample end of the device (i.e. the end which is pointed away from the skin). Forward and rearward will, likewise, be understood to refer to the directions orientated towards the front and rear of the device.

The terms axial, radial and circumferential are used herein to conveniently refer to the general directions relative to the longitudinal direction of the device (or components thereof). The skilled person will, however, appreciated that these terms are not intended to be narrowly interpreted (and for example, the device may have a non-circular and/or irregular form). Typically, regardless of the specific and aesthetic design of the lancing device the device will be generally elongate and have a longitudinal axis that is generally aligned with the lancing needle and the forward/rearward direction of travel of the lancet in use, as such, the longitudinal axis of the device will substantially coincide with (or be parallel to) the axial direction of the lancet.

Referring to FIGS. 1 to 8, a blood sampling device 1 according to an exemplary embodiment of the present invention includes a plastic housing 10 containing a lancet 50 and a spring 70. The lancet 50 comprises a lancet body 60 moulded around a needle 52, the sharp tip 53 of the needle 52 projecting from a forward surface 63 of the lancet body 60. An elongate cap 90 is integrally moulded with the forward surface 63 of the lancet body 60 such that the lancet needle 52 is initially concealed within the elongate cap 90.

The housing 10 is also integrally moulded in two side-by-side channel-like upper and lower halves 20 and 30 with a thin web or a set of webs bridging adjacent sides and forming a hinge (not shown). These halves 20 and 30 are subsequently folded together to form an elongate cavity 40 within which the lancet 50 and the spring 70 are located. During assembly the halves 20 and 30 are adhered or welded to encase the lancet 50 and the spring 70. Once assembled, the upper and lower halves 20 and 30 are configured to remain fitted together throughout the duration of the useable lifetime of the blood sampling device 1. The rear end of the housing 10 is closed, but the forward ends of the halves 20 and 30 have semi-circular cut-outs which combine to form an aperture 41.

The upper half 20 of the housing 10 comprises an integrally formed finger 21 which protrudes into the cavity 40. The finger 21 is spaced apart from the rear end of the housing 10 and the rear end of the spring 70 is retained between the finger 21 and the rear end of the housing 10. The lancet body 60 is elongate with a substantially cruciform longitudinal side cross-section prior to a notch 64 and a rear bulbous tail 61. The lancet body 60 comprises a pair of radial wings 62a and 62b which project at an angle of roughly 90° from the immediately adjacent surfaces of the lancet body 60. The lancet 50 is formed of a rear portion (rearward of the radial wings 62a and 62b) and a forward portion (including and forward of the radial wings 62a and 62b). The forward end of the spring 70 coils around the bulbous tail 61 and is retained captive thereon by a snap fit engagement with the notch 64. The spring 70 therefore acts between the finger 21 and the lancet body 60 to bias the lancet 50 forwardly in the housing 10.

The upper half 20 of the housing 10 comprises an integrally formed lip 25 which projects into the cavity 40 at an angle of roughly 90° relative to the immediately adjacent internal surface of the upper half 20 of the housing 10. When assembled, the lancet body 60 is biased forwardly in the housing 10 by the spring 70 such that the forward surface of the upper radial wing 62a is urged against the rear surface of the lip 25. As both the upper radial wing 62a and the lip 25 project at an angle of roughly 90° from their respective components, this abutment prevents forward movement of the lancet 50. The cavity 40 has a convex profile on the portion of the internal surface of the lower half 30 (i.e. the lower wall of the cavity 40) of the housing opposing the lip 25 which extends from the rear end of the housing 10 to at least the length of the upper wing 62a of the lancet body 60 forwardly of the front surface of the lip 25. The convex portion of the lower wall of the cavity 40 comprises a deflection surface 31 at the forward end thereof. The deflection surface 31 is a sloped surface at an angle of roughly 150° relative to the immediately rearward portion of the lower wall of the cavity 40.

The housing 10 also comprises a pair transverse projections 27 and 37 spaced rearwardly of the aperture 41 and extending from the upper an lower halves 20 and 30 respectively into the cavity 40, thus forming a constriction 42 (i.e. a portion of reduced height) in the cavity 40. These transverse projections 27 and 37 limit forward movement of the lancet body 60 as the span of the upper and lower radial wings 62a and 62b is greater than the vertical span of this constriction 42. This therefore limits forward movement of the sharp tip 53 of the needle 52 in the pricking direction.

The upper half 20 of the housing 10 comprises an integrally formed trigger 22 having an upper surface which protrudes upwardly from the upper half 20 of the housing 10 and comprises a finger pad 23 forming the upper surface thereof which is textured to improve grip when depressed by the user and a lower surface 24 forming a portion of the upper wall of the elongate cavity 40. The plastics material of which the housing 10 is moulded allows the trigger 22 to be flexed inward into the cavity 40 to contact the upper radial wing 62a of the lancet body 60, as will be discussed in further detail below. The trigger is positioned rearwardly of, and adjacent to, the lip 25, with a gap 26 provided therebetween.

Figure 1:
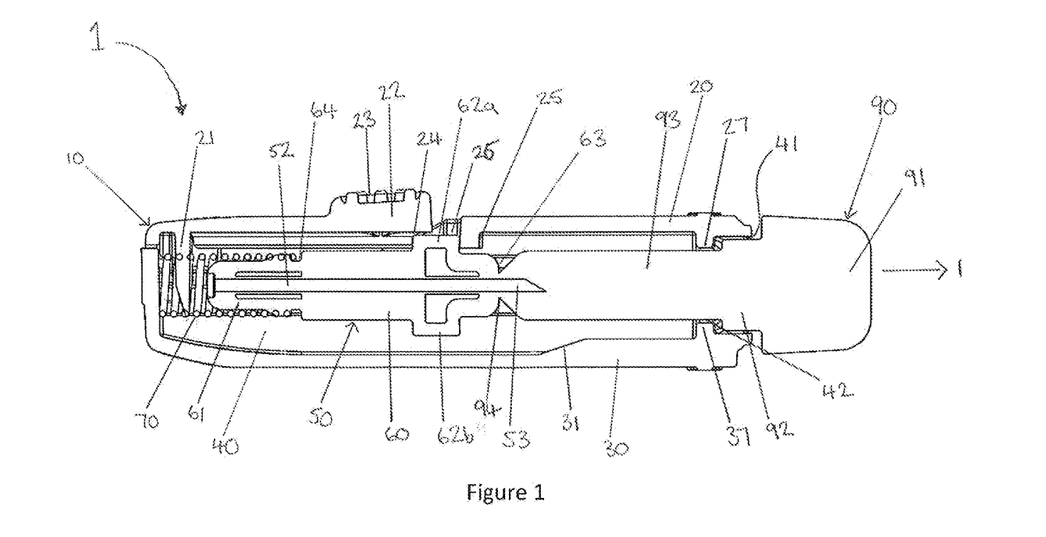
FIG. 1 is a schematic longitudinal cross sectional view of a blood sampling device according to an exemplary embodiment of the present invention in an assembled configuration.

Referring now to FIG. 1, when the blood sampling device 1 is in an initial assembled configuration, the spring 70 is compressed, urging the lancet body 60 forwardly in a pricking direction indicated by arrow P. However, the forward surface of the upper radial wing 62a of the lancet body 60 is abutting the rear surface of the lip 25, preventing forward movement of the lancet body 60 (i.e. the lancet body 60 is in an obstructed position). The trigger 22 is in a rest position and the upper surface of the upper radial wing 62a is adjacent to but not contacting the lower surface 24 of the trigger 22. In this initial position, the lancet body 60 is substantially aligned with the longitudinal axis of the housing 10.

The elongate cap 90 has a graspable portion 91 located externally of the housing 10, connected to an intermediate portion 92 bridging the aperture 41 of the housing 10. The intermediate portion 92 is connected to a stem 93 which extends into the housing 10 and has a frangible connection 94 with the forward surface 63 of the lancet body 60 such that the sharp tip 53 of the needle 52 is initially concealed within the stem 93. The intermediate portion 92 of the cap has a complementary cross-section to the aperture 41 and the stem has a complementary cross-section to the constriction 42 of the cavity 40. This means that the cap 90 cannot be moved up and down, or otherwise angularly moved, within the housing 10. Due to the frangible connection 94 between the stem 93 of the cap 90 with the forward surface 63 of the lancet body 60, the lancet body 60 also cannot be moved up and down, or otherwise angularly moved, within the housing 10. As the upper surface of the upper radial wing 62a is adjacent to the lower surface 24 of the trigger 22, this also means that the trigger 22 cannot be depressed. Thus, there is no way of deflecting the lancet 50 transversely within the cavity 40 of the housing 10 from an obstructed position to a passage position while the cap 90 is frangibly connected to the lancet body 60 (i.e. the lancet body 60 cannot be deflected until the cap 90 is removed from the sharp tip 53 of the needle 50).

Figure 3:
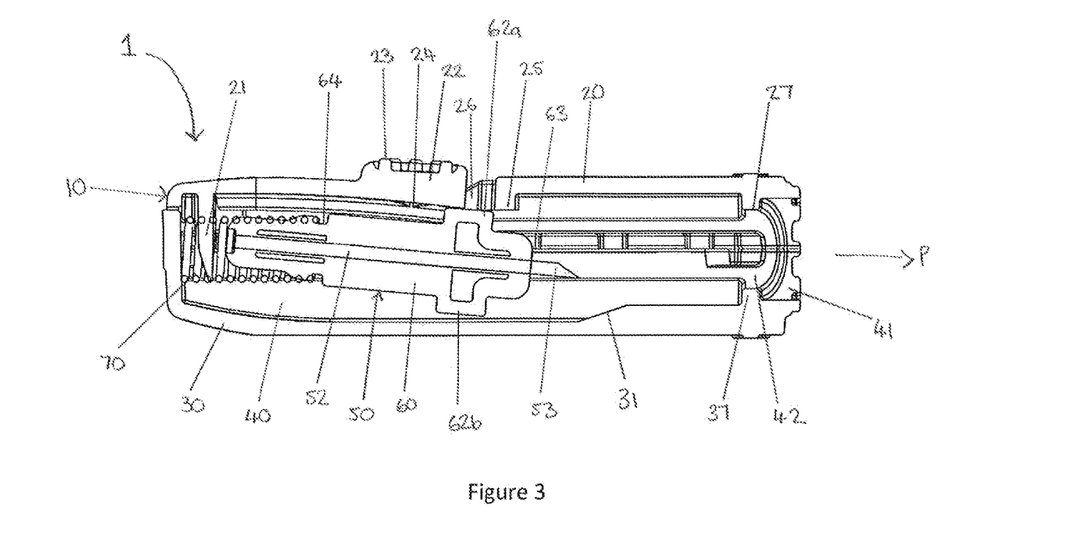
FIG. 3 is a longitudinal cross-sectional view of the blood sampling device of FIG. 1 during actuation of the trigger member.

If a user were to try and pull the cap 90 forwardly in the pricking direction P to remove it from the housing 10 before the connection 94 between the cap 90 and the lancet body 60 is completely severed, the lancet body 60 would be prevented from firing prematurely due to the abutment between the forward surface of the upper radial wing 62a of the lancet body 60 and the rear surface of the lip 25. As such, transverse deflection of the lancet body 60 within the cavity 40 so that it is no longer abutting the lip 25 is required in order to fire the lancet 50. This deflection is carried out by depression of the trigger 22 from the rest position (FIG. 1) to a fire position (FIG. 3). The trigger 22 cannot be depressed into the fire position until the cap 90 has been removed from the sharp tip 53 of the lancet 50. As such, the lancet 50 cannot be fired until the cap 90 is removed from the sharp tip 53 of the lancet 50, preventing premature activation of the blood sampling device 1.

The cap 90 may be removed by holding the graspable portion 91 and twisting it relative to the housing 10 about the direction of pricking P. The twisting action breaks the frangible connection 94 such that the cap 90 is freeable from the housing 10. Withdrawal of the cap 90 in the pricking direction P exposes the sharp tip 53 inside the housing 10. Thus, until this time the needle 52 is hermetically sealed prior to use.

Figure 2:
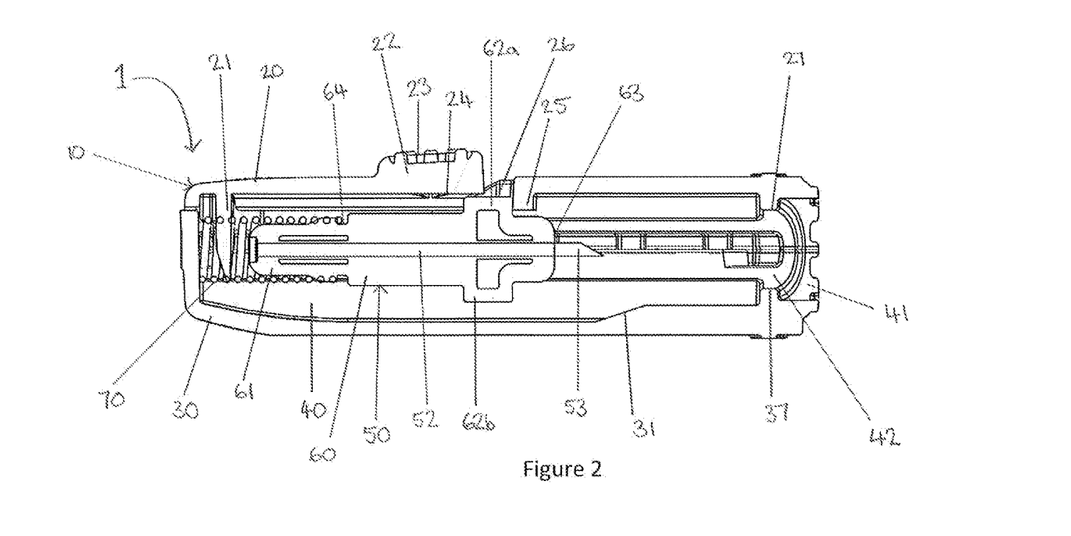
FIG. 2 is a longitudinal cross-sectional view of the blood sampling device of FIG. 1 in a primed configuration with the cap removed.

Referring to FIG. 2, once the cap 90 has been removed from the housing 10, the blood sampling device 1 is primed and the lancet 50 is ready to be fired. The cap 90 is no longer preventing deflection of the lancet body 60 within the cavity 40. In use, the user will hold the forward end of the blood sampling device 1 against the skin, position their thumb or finger on the finger pad 23 and depress the trigger 22 (FIG. 3). This is enabled because the cap 90 is no longer preventing deflection of the lancet 50. Initial depression of the trigger 22 flexes it inward into the cavity 40 such that the lower surface 24 of the trigger 22 contacts the upper radial wing 62a of the lancet body 60. Further depression of the trigger 22 forces the upper radial wing 62a (and therefore the entirety of the forward portion of the lancet body 60) downwards within the cavity 40. When the trigger 22 is depressed into the fire position, the forward surface of the upper radial wing 62a is no longer abutting the rear surface of the lip 25 (i.e. the forward surface of the upper radial wing 62a and the rear surface of the lip 25 are not vertically aligned). The lancet body 60 is angularly positioned relative to the longitudinal axis of the housing 10 and the lancet body 60 is in a passage position.

Figure 4:
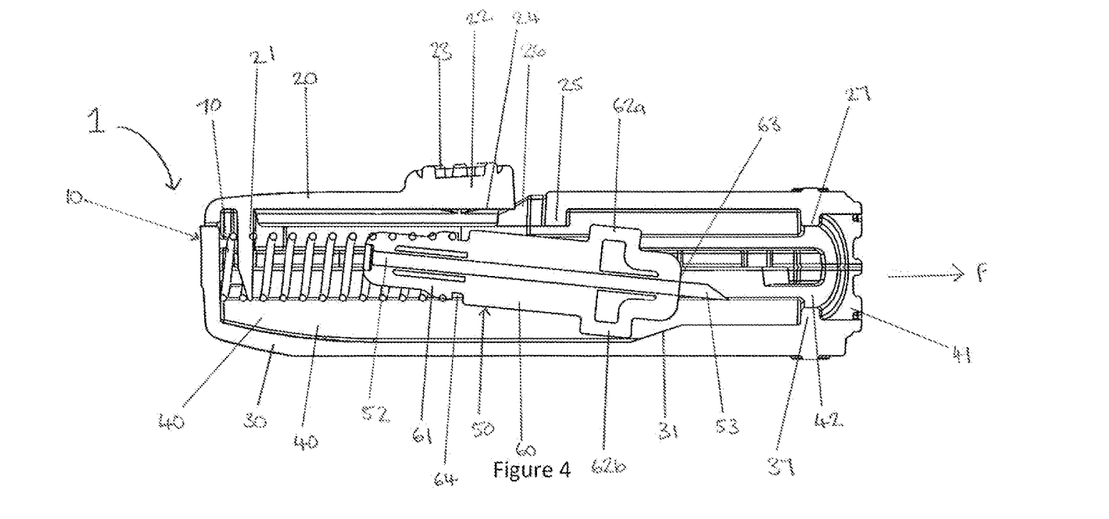
FIG. 4 is a longitudinal cross-sectional view of the blood sampling device of FIG. 1 when the lancet body is in a passage position during firing.
Figure 5:
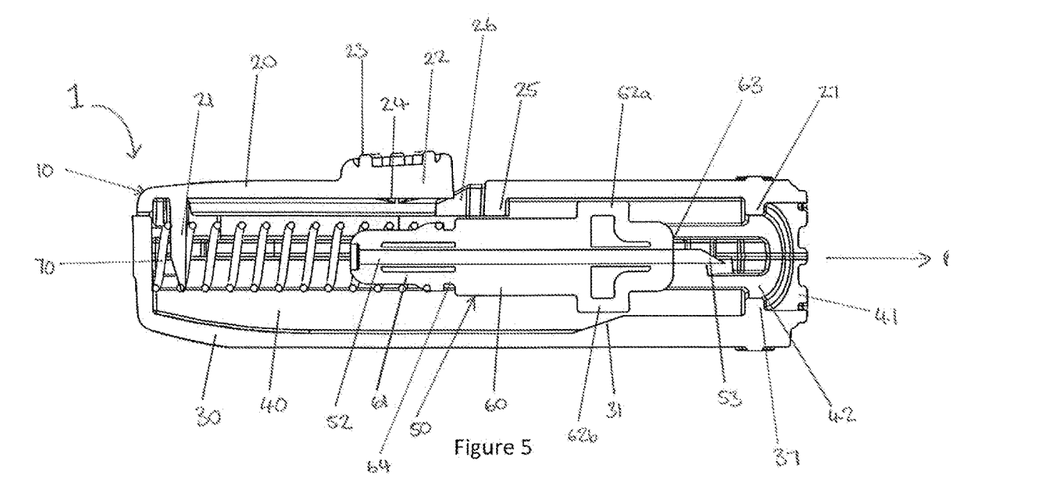
FIG. 5 is a longitudinal cross-sectional view of the blood sampling device of FIG. 1 when the lancet body is in a blocked position during firing.

Referring to FIG. 4, once the forward portion of the lancet body 60 has been vertically deflected within the housing out of abutment with the rear surface of the lip 25, there is no obstacle blocking forward movement of the lancet body 60 within the cavity 40 (i.e. the lancet body 60 is in a passage position). Thus, the spring 70 urges the lancet body 60 forwardly in the pricking direction P. The forward surface of the lower radial wing 62b contacts the sloped deflection surface 31, deflecting the forward portion of the lancet body 60 back into alignment with the longitudinal axis of the housing 10 (FIG. 5). The upper radial wing 62a projects a sufficient distance upwardly from the rearward portion of the lancet body 60 that once the upper radial wing 62a has cleared the lip 25, the rearward portion of the lancet body 60 does not contact the lip 25 throughout the remainder of the forward movement of the lancet body 60.

Figure 6:
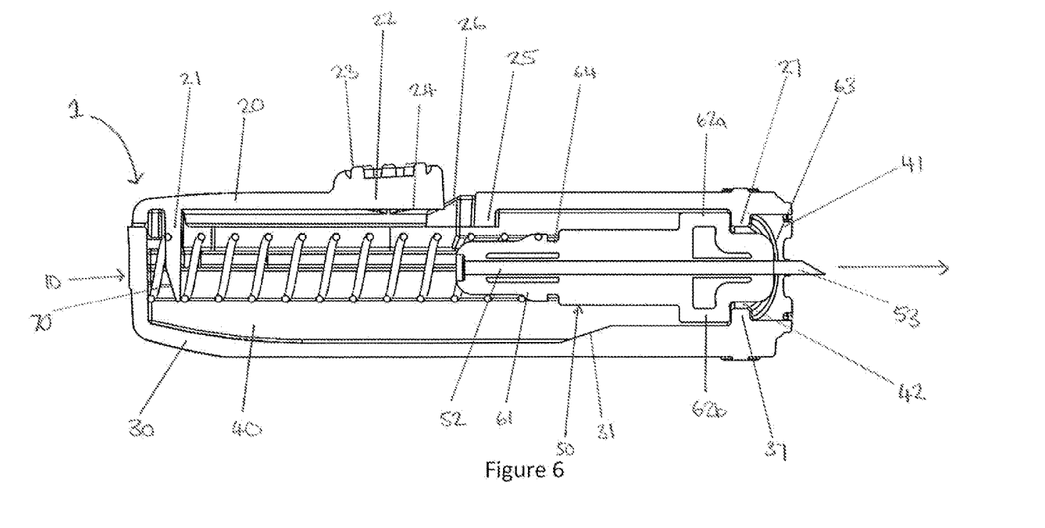
FIG. 6 is a longitudinal cross-sectional view of the blood sampling device of FIG. 1 in a lancing position.

The lancet body 60 continues to travel forwardly within the cavity 40 under the bias of the spring 70 until the upper and lower radial wings 62a and 62b contact the transverse projections 27 and 37 respectively, preventing further forward movement of the lancet body 60. The sharp tip 53 protrudes from the forward end of the housing 10, to puncture the skin of the user, drawing a sample of blood from the user.

Figure 7:
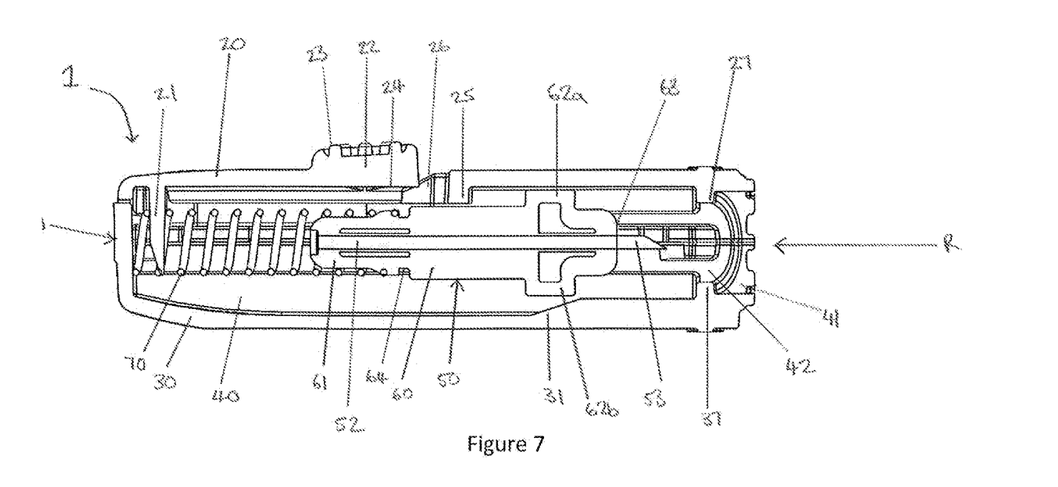
FIG. 7 is a longitudinal cross-sectional view of the blood sampling device of FIG. 1 with the lancet body in a safe position after completion of firing.

Referring to FIG. 7, the forward momentum of the lancet 50 over-stretches the spring 70. Thus, after the momentary projection of the sharp tip 53 from the forward end of the housing 10, the lancet 50 rebounds in the rebound direction illustrated by arrow R so that the sharp tip 53 is returned safely within the housing 10 to prevent accidental injury but with the lancet 50 well forward of the initial primed position. The spring 70 is now in equilibrium and therefore does not exert a force on the lancet 50 in either the rearward or forward directions.

Figure 8:
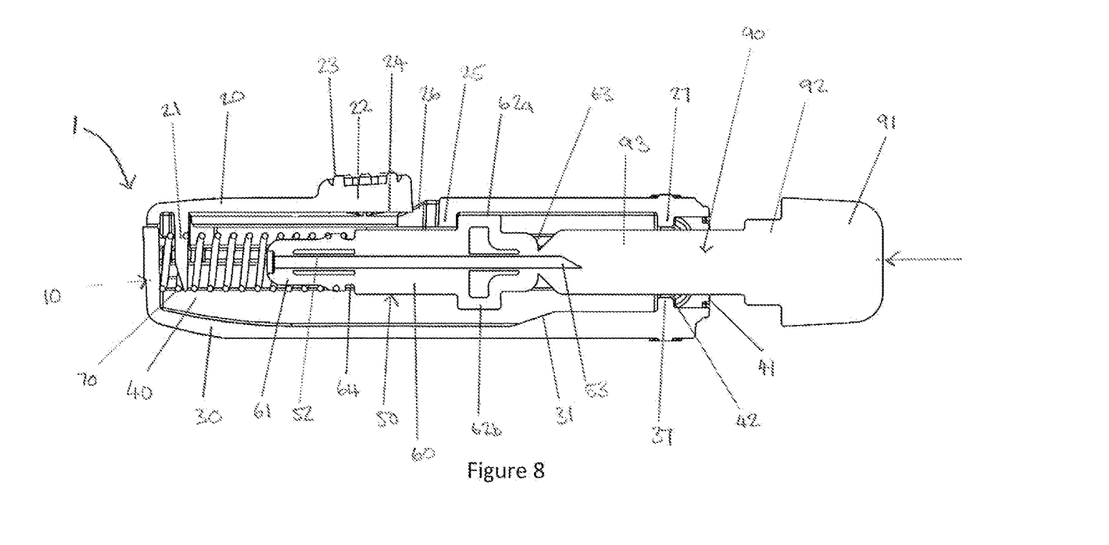
FIG. 8 is a longitudinal cross-sectional view of the blood sampling device of FIG. 1 with the lancet body in a safe position after completion of firing showing attempted replacement of the cap.

Referring to FIG. 8, after completion of lancing, the user will remove the blood sampling device 1 from the surface of the skin. As noted above, the sharp tip 53 will be safely positioned within the cavity 40 of the housing 10. However, the user may try to re-prime the device such that it can be re-used by re-inserting the cap 90 into the housing 10 and applying a force in the rebound direction R against the cap 90 to urge the lancet body 60 rearwardly. However, the lip 25 prevents re-priming of the device. Rearward movement of the lancet body 60 within the cavity 40 is enabled until the rearward surface of the upper radial wing 62a contacts the forward surface of the lip 25. This abutment prevents further rearward movement of the lancet body 60. The spring 70 is not sufficiently compressed in this position to re-fire the lancet body 60 so that the sharp tip 53 projects beyond the forward end of the housing 10. Thus, the device cannot be re-used and is rendered safe from accidental injury.

It is noted that the forward surface of the lip 25, the rear surface of the lip 25, the forward surface of the upper radial wing 62a, the rearward surface of the upper radial wing 62a, the forward surface of the lower radial wing 62b and the rear surface of the transverse projections 27 and 37 all project at an angle of roughly 90° from the respective surface immediately adjacent thereto. However, the invention is not limited in this regard. The skilled person would understand that each of these surfaces may project at any angle sufficient to prevent relative movement as appropriate. Similarly, the deflection 31 surface may project at any angle sufficient to deflect the lancet body 60 without preventing further forward movement of the lancet body 60.

It will be apparent to a person skilled in the art that modifications and variations can be made to the described embodiment without departing from the scope of the invention as defined by the appended claims.

The invention claimed is:

1. A blood sampling device comprising:
    a housing having a forward end with an opening therein;
    a lancet comprising a lancet body having a first radial wing and a second, rigid radial wing, the lancet body supporting a lancet needle at a forward end thereof, the lancet being moveably mounted within said housing;
    an urging member for urging the lancet forwardly, in use, relative to the housing between a rearward primed position in which the lancet needle is within the housing and a forward lancing position in which a tip of the lancet needle projects forwardly from the opening at the forward end of the housing; wherein
    said housing defines a cavity, the cavity including a passageway along which the lancet travels between the rearward primed position and the forward lancing position and the housing having an abutment member extending into the cavity defining a fixed abutment surface for holdingly engaging a front surface of the first radial wing of the lancet in the rearward primed position; and
    the blood sampling device further comprising a trigger moveable from a rest position to a fire position to release the lancet for forward movement, wherein the trigger contacts the first radial wing to deflect the lancet body in a direction generally transverse to a longitudinal axis of the housing such that the entire lancet body rotates so that the first radial wing is no longer engaged with the fixed abutment surface allowing the lancet body to move forwardly past the fixed abutment surface; and
    the housing comprising a deflection surface positioned in and projecting into the passageway forwardly of the abutment surface, the deflection surface being configured to contact the second rigid radial wing to rotate the entire lancet, after release and after the lancet forwardly passes the fixed abutment surface.

2. The blood sampling device as claimed in claim 1, wherein the trigger deflects the lancet body angularly relative to the longitudinal axis of the housing.

3. The blood sampling device as claimed in claim 1, wherein the blood sampling device further comprises a removable safety cap for at least partially covering the tip of the lancet needle; and
    wherein the removable safety cap is configured to prevent firing of the blood sampling device prior to removal of the safety cap from the tip of the lancet needle.

4. The blood sampling device as claimed in claim 3, wherein prior to removal, the safety cap supports the lancet body within the blood sampling device such that it cannot be deflected transversely past the fixed abutment surface.

5. The blood sampling device as claimed in claim 4, wherein the safety cap comprises a portion which extends through the opening at the forward end of the housing and rearwardly along the passageway to the forward end of the lancet body; and wherein said portion prevents transverse movement of the lancet within the housing when the safety cap is attached thereto.

6. The blood sampling device according to claim 3, wherein the safety cap is forwardly removable such that the safety cap may be withdrawn from the passageway to ready the blood sampling device.

7. The blood sampling device according to claim 3, wherein the safety cap has a graspable portion external to the housing and a stem substantially within the housing.

8. The blood sampling device according to claim 1, wherein the trigger comprises an externally accessible portion and wherein depression of the externally accessible portion moves the trigger from the rest position to the fire position.

9. The blood sampling device according to claim 1, wherein movement of the trigger from the rest position to the fire position is a generally transverse movement relative to the longitudinal axis of the housing.

10. The blood sampling device according to claim 1, wherein the trigger is an integral component of the housing.

11. The blood sampling device according to claim 10, wherein the housing is an integral moulding with two halves hinged together, the trigger being formed on one of the two halves.

12. The blood sampling device according to claim 1, wherein the blood sampling device further comprises means for preventing rearward movement of the lancet body from the forward lancing position to the rearward primed position.

13. The blood sampling device according to claim 1, wherein the housing comprises a second abutment surface within the passageway configured to prevent rearward movement of the lancet body from the forward lancing position to the rearward primed position.

14. The blood sampling device according to claim 13, wherein the second abutment surface is located sufficiently rearwardly of the opening such that the tip of the lancet needle is contained within the housing after use.

15. The blood sampling device according to claim 13, wherein the lancet body comprises an abutment surface configured to cooperate with the second abutment surface of the housing to prevent rearward movement of the lancet body from the forward lancing position to the rearward primed position.

16. The blood sampling device according to claim 1, wherein the abutment member has a rear surface which defines the abutment surface and a front surface, the front surface being configured to engage the lancet body to prevent rearward movement thereof from the forward lancing position to the rearward primed position.

17. The blood sampling device according to claim 1, wherein the abutment member has a rear surface which defines the abutment surface and a front surface, the front surface being configured to engage the lancet body to prevent rearward movement thereof from the forward lancing position to the rearward primed position, and the deflection surface is configured to deflect the lancet body angularly relative to the longitudinal axis of the housing to a blocked position in which the lancet body cannot move rearwardly back past the front surface of the abutment member.

18. The blood sampling device according to claim 1, wherein the lancet body comprises a deflection surface configured to cooperate with the deflection surface of the housing.

19. The blood sampling device according to claim 13, wherein the lancet body comprises a rear surface configured to engage the second abutment surface of the housing.

20. The blood sampling device according to claim 1, wherein the cavity and second radial wing are dimensioned such that the second radial wing is spaced from an inner wall of the cavity when the abutment surface engages the front surface of the first radial wing.

* * * * *